US009289464B2

(12) United States Patent
Loos (10) Patent No.: US 9,289,464 B2
(45) Date of Patent: Mar. 22, 2016

(54) METHOD FOR DIAGNOSING AND TREATING NIS-EXPRESSING CARCINOMAS AND METASTASES

(76) Inventor: Ulrich Loos, Ulm/Donau (DE)

( * ) Notice: Subject to any disclaimer, the term of this patent is extended or adjusted under 35 U.S.C. 154(b) by 3012 days.

(21) Appl. No.: 10/518,413

(22) PCT Filed: Jun. 18, 2003

(86) PCT No.: PCT/EP03/06435
§ 371 (c)(1),
(2), (4) Date: Dec. 5, 2005

(87) PCT Pub. No.: WO03/107001
PCT Pub. Date: Dec. 24, 2003

(65) Prior Publication Data
US 2006/0104897 A1    May 18, 2006

(30) Foreign Application Priority Data

Jun. 18, 2002   (DE) .................................. 102 27 136

(51) Int. Cl.
| A61K 51/00 | (2006.01) |
| A61K 31/203 | (2006.01) |
| A61K 31/426 | (2006.01) |
| A61K 31/4439 | (2006.01) |
| A61K 38/15 | (2006.01) |
| G01N 33/574 | (2006.01) |

(52) U.S. Cl.
CPC .......... *A61K 38/15* (2013.01); *G01N 33/57407* (2013.01); *G01N 33/57415* (2013.01); *G01N 33/57442* (2013.01)

(58) Field of Classification Search
None
See application file for complete search history.

(56) References Cited

U.S. PATENT DOCUMENTS

| 5,654,333 A * | 8/1997 | Samid ........................... 514/538 |
| 5,811,119 A * | 9/1998 | Mehta et al. .................. 424/450 |
| 5,814,647 A * | 9/1998 | Urban et al. .................. 514/369 |
| 6,673,823 B2 * | 1/2004 | Heaney et al. ................ 514/369 |

OTHER PUBLICATIONS

Schmutzer, C., "Regulation of the sodium/iodide symporter by retinoids—a review", 2001, Experimental and Clinical Endocrinology and Diabetes, 109, pp. 41-44.*
Mandell, R.B., et al., "Radioisotope Concontrator Gene Therapy Using the Sodium/Iodine Symporter Gene", 1999, Cancer Research, 59, pp. 661-668.*
Mehta, R.G., et al., "A Ligand of Peroxisome Proliferator-Activated Receptor gamma, Retinoids, and Prevention of Preneoplastic Mammary Lesions", 2000, Journal of the National Cancer Institute, 92:5, pp. 418-423.*
Buommino, E., et al., "Sodium butyrate/retinoic acid costimulation . . . ", 2000, Journal of Molecular Endocrinology, 24, pp. 83-94.*
Kinoshita, M., et al., "Butyrate reduces colonic paracellular . . . ", 2002, Biochemical and Biophysical Research Communications, 293, pp. 827-831.*
Simon, D., et al., "Rediffentiation Therapy with Retinoids . . . ", 1998, World J. Surgery, 22, pp. 569-574.*
Tontonoz, P., et al., "Terminal differentiation of human . . . ", 1997, PNAS, 94, pp. 237-241.*
Elstner, E., et al., "20-epi-Vitamin D3 Analogues: A Novel Clas of Potent Inhibitors of Proliferation and Inducers of Diferentiation of Human Breast Cancer Cel Lines'", Cancer Research, 1995, pp. 2822-2830.*
Elstner, E., et al., "1a,25-Dihydroxy-20-Epi-Vitamin DJ: An Extraordinarily Potent Inhibitor of Leukemic Cell Growth in Vitro", Blood, 1994, pp. 1960-1967.*
Media "Alpha Minimal Medium", printed Jan. 25, 2015, accessed from: "http://www.biochrom.de/fileadmin/user_upload/service/produktinformation/englisch/BC_catalogue_34_Alpha_Medium.pdf". pp. 34.*
Elstner, E., et al., "Ligands for peroxisome proliferator-activated receptory γ and retinoic acid receptor inhibit growth and induce apoptosis of human breast cancer cells in vitro and in BNX mice", *Proc. Natl. Acad. Sci. USA*, vol. 95, pp. 8806-8811, (1998).
Mehta, R.G., et al., "A Ligand of Peroxisome Proliferator-Activated Receptor γ , Retinoids, and Prevention of Preneoplastic Mammary Lesions", *Journal of the National Cancer Institute*, vol. 92, No. 5, pp. 418-423, (2000).
Sato, M., et al., "Synergistic Potentiation of Thiazolidinedione-Induced ST 13 Preadipocyte Differentiation by RAR Synergists", *Biochemical and Biophysical Research Communications*, vol. 280, pp. 646-651, (2001).
Westin, S., et al., "Interactions controlling the assembly of nuclear-receptor heterodimers and co-activators", *Nature*, vol. 395, pp. 199-202, (1998).
Schulman, I.G., et al., "Transactivation by Retinoid X Receptor-Peroxisome Proliferator-Activated Receptor γ (PPARγ) Heterodimers: Intermolecular Synergy Requires Only the PPAR γ Hormone-Dependent Ativation Function", *Molecular and Cellular Biology*, vol. 18, No. 6, pp. 3483-3494, (1998).
Kogai, T., et al., "Differential Regulation of the Human Sodium/Iodide Symporter Gene Promoter in Papillary Thyroid Carcinoma Cell Lines and Normal Thyroid Cells", *Endocrinology*, vol. 142, No. 8, pp. 3369-3379, (2001).

(Continued)

*Primary Examiner* — Michael G Hartley
*Assistant Examiner* — Lance Rider
(74) *Attorney, Agent, or Firm* — Nath, Goldberg & Meyer; Gary M. Nath; Tanya E. Harkins (57) ABSTRACT

The present invention relates to a method for diagnosing and/or treating sodium-iodide symporter (NIS)-expressing primary carcinomas and metastases, preferably glandular carcinomas, in particular carcinomas of the thyroid, of the salivary gland, of the uterus and carcinomas of the breast, and to a pharmacological composition comprising substances which induce and/or increase the expression or function of the NIS symporter and, as a consequence, increase iodide uptake into the cells, and to corresponding uses. This can be used for an efficient tumor-specific radioiodide uptake in diagnosis and therapy of said carcinomas and metastases.

30 Claims, 2 Drawing Sheets

(56) References Cited

OTHER PUBLICATIONS

Filetti, S., et al., "Sodium/iodide symporter: a key transport system in thyroid cancer cell metabolism". *European Journal of Endocrinology*, vol. 141, pp. 443-447, (1999).

Kitazono, M., et al., "Low Concentrations of the Histone Deacetylase Inhibitor, Depsipeptide (FR901228), Increase Expression of the Na$^+$/I$^-$ Symporter and Iodine Accumulation in Poorly Differentiated Thyroid Carcinoma Cells", *The Journal of Clinical Endocrinology & Metabolism*, vol. 86, No. 7, pp. 3430-3435, (2001).

Tanosaki, S., et al., "Effect of ligands of nuclear hormone receptors on sodium/iodide symporter expression and activity in breast cancer cells", *Breast Cancer Research and Treatment*, vol. 79, pp. 335-345, (2003).

Carrasco, N., "Iodide transport in the thyroid gland", *Biochimica et Biophysica Acta*, vol. 1154, pp. 65-82, (1993).

De La Vieja, A., et al., "Molecular Analysis of the Sodium/Iodide Symporter: Impact on Thyroid and Extrathyroid Pathophysiology", *Physiological Reviews*, vol. 80, No. 3, pp. 1083-1105, (2000).

Heufelder, A.E., "Sodium Iodide Symporter-Based Strategies for Diagnosis and Treatment of Thyroidal and Nonthyroidal Malignancies", *Thyroid*, vol. 11, No. 9, pp. 839-847, (2001).

Inoue, K., "Expression of Peroxisome Proliferator-Activated Receptor (PPAR)—γ in Human Lung Cancer", *Anticancer Research*, vol. 21, pp. 2471-2476, (2001).

Kilgore, M.W., "MCF-7 and T47D human breast cancer cells contain a functional peroxisomal response", *Molecular and Cellular Endocrinology*, vol. 129, pp. 229-235, (1997).

Kogai, T., "Retinoic acid induces sodium/iodide symporter gene expression and radioiodide uptake in the MCF-7 breast cancer cell line" *PNAS*, vol. 97, No. 15, pp. 8519-8524, (2000).

Braverman, L.E., et al., (Ed.), "Chapter 80: Carcinoma of Follicular Epithelium", *Werner and Ingvar's: The Thyroid*, 7$^{th}$ Ed., Lippincott-Raven Publishers: New York, pp. 922-944, (1996).

Murphy, G.J., et al., "PPAR—γ agonists: therapeutic role in diabetes, inflammation and cancer", *TiPS*, vol. 21, pp. 469-474, (2000).

Nwankwo, J.O., et al., Peroxisome proliferator-activated receptor—γ expression in human malignant and normal brain, breast and prostate-derived cells, *Prostaglandins, Leukotrienes and Essential Fatty Acids*, vol. 64, No. 4 and 5, pp. 241-245, (2001).

Riedel, C., et al., "Journey of the iodide transporter NIS: from its molecular identification to its clinical role in cancer", *Trends in Biochemical Sciences*, vol. 26, No. 8, pp. 490-496, (2001).

Sugiyama, Y., et al., "Mechanisms of thiazolidinedione derivatives for hypoglycemica and insulin sensitizing effects", *Nippon Rinsho*, vol. 58, No. 2, pp. 370-375, (2000).

Tazebay, U.H., et al., "The mammary gland iodide transporter is expressed during lactation and in breast cancer", *Nature Medicine*, vol. 4, No. 8, pp. 871-878, (2000).

Titcomb, M.W., et al., "Sensitive and Specific Detection of Retinoid Receptor Subtype Proteins in Cultured Cell and Tumor Extracts", *Molecular Endocrinology*, vol. 8, No. 7, pp. 870-877, (1994).

Ide, T., et al., "Cross-Talk between Peroxisome Proliferator-Activated Receptor (PPAR) α and Liver X Receptor (LXR) in Nutritional Regulation of Fatty Acid Metabolism. II. LXRs Suppress Lipid Degradation Gene Promoters through Inhibition of PPAR Signaling", *Molecular Endocrinology*, vol. 17, No. 7, pp. 1255-1267, (2003).

Behr, M., et al., "Periodically hyperthyroid phenotype in thyroid hormone resistance is associated with mutation D322N in the thyroid hormone receptor β gene: Transcriptional properties of the mutant and the role of retinoid X receptor", *Exp Clin Endocrinol Diabetes*, vol. 104, Suppl. 4, pp. 111-116, (1996).

Schumtzler, C., "Regulation of the sodium/iodide symporter by retinoids—a review", *Exp. Clin. Endocrinol. Diabetes*, vol. 109, pp. 41-44, (2001).

Schumtzler, C., et al., "Treatment of Prostate Cancer by Radioidine Therapy after Tissue-specific Expression of the Sodium Iodide Symporter", *Cancer Research*, vol. 60, pp. 6526-6530, (2000).

Spitzweg, C., et al., "In vivo sodium iodide symporter gene therapy of prostate cancer", *Gene Therapy*, vol. 8, pp. 1524-1531, (2001).

Spitzweg, C., et al., "Treatment of Prostate Cancer by Radioiodine Therapy after Tissue-specific Expression of the Sodium Iodide Symporter", *Cancer Research*, vol. 60, pp. 6526-6530, (2000).

\* cited by examiner

METHOD FOR DIAGNOSING AND TREATING NIS-EXPRESSING CARCINOMAS AND METASTASES

The present invention relates to a method for diagnosing and/or treating sodium-iodide symporter (NIS)-expressing primary carcinomas and metastases, preferably glandular carcinomas, in particular carcinomas of the thyroid, of the salivary gland, of the uterus and carcinomas of the breast, and to a pharmacological composition comprising substances which induce and/or increase the expression or function of NIS and, as a consequence, increase iodide uptake into the cells, and to corresponding uses. This is used for an efficient organ-specific radioiodide uptake in diagnosis and therapy of said carcinomas and metastases.

Some methods for diagnosing and treating primary glandular carcinomas and metastases of glandular carcinomas such as of the thyroid, of the salivary gland, of the uterus and carcinomas of the breast are known in the art. Known diagnostic methods include sonography, mammography and magnetic resonance imaging. The disadvantages of these methods are in particular that they must be employed in combination in order to increase the specificity of the diagnosis. Ordinarily, a core needle biopsy follows and may lead to dissemination of cancer cells and thus to iatrogenic metastasis. The definitive diagnosis must be made by surgical resection or core needle biopsy and histological examination of the nodule, and it often emerges that the nodule is benign. The elaborate diagnostic procedure frequently results in loss of time and unnecessary surgical procedures.

Primary therapy of said tumors usually consists of surgical resection of the primary carcinoma. Depending on the size of the tumor (e.g. larger than 2 cm in diameter) or evidence of lymph node involvement, especially in carcinoma of the breast, additionally the ipsilateral axillary lymph nodes are removed, with, where appropriate, irradiation of the suprarregional area. Investigations are performed postoperatively to detect or exclude remote metastases, i.e. for example an upper abdominal sonography, a chest radiograph and a skeletal scintigram. Only metastases above a certain size are identified in these cases. Smaller metastases, i.e. for example smaller than 0.5 cm in diameter, so-called micrometastases, are often not identified. In the bone scintigram, degenerative or inflammatory changes may lead to false-positive findings. In the event of metastases, chemotherapy is carried out, but may have considerable side effects. This treatment is only palliative and leads merely to a small increase in lifespan.

One object of the present invention is to provide a method for the rapid, specific and reliable diagnosis and for the efficient treatment of carcinomas and metastases, in particular of primary glandular carcinomas and metastases of glandular carcinomas, especially of carcinomas of the thyroid, of the salivary gland, of the uterus, and of carcinomas of the breast, a pharmacological composition for the therapy, and an in vitro diagnostic system on resected tissue for the diagnosis and assessability of the possibility of treating said carcinomas.

To achieve this object, the invention firstly proposes a method having the features specified in claim 1. Further developments of the method, pharmacological compositions, and corresponding uses are the subject matter of the other dependent and independent claims 2 to 39, whose wording is incorporated in the description by reference.

The abovementioned aim is achieved according to the invention by a method in which there is organ-specific stimulation of enhanced iodide uptake through inducing or increasing NIS gene expression and function in said types of tumors, which uptake can be utilized for specific diagnosis and/or targeted therapy.

The sodium-iodide symporter (NIS) is responsible for active iodide uptake in the thyroid. The iodine is used in the follicle cells of the thyroid for the purpose of biosynthesizing thyroid hormones (N. Carrasco, Biochim Biophys Acta. 1993 Jun. 8; 1154 (1): 65-82). NIS expression has been utilized for decades for diagnosing and treating differentiated thyroid carcinomas based on the administration of radioiodide (E. L. Mazzaferri, 1996 in The Thyroid, eds. L. E. Braverman and R. D. Utiger (Lippincott-Raven, Philadelphia), pp. 942-945). NIS is also expressed, in some cases functionally, in many extrathyroid tissues such as kidneys, placenta, salivary glands, gastric mucosa and lactating mammary gland, as has been demonstrated at the mRNA and protein levels (A. De La Vieja et al., Physiol Rev. 2000 July. 80 (3): 1083-105).

NIS has been detected in 80% of human mammary gland cancers by means of immunohistochemistry (U. H. Tazebay et al., Nat Med. 2000 Aug. 6 (8): 871-8), without, however, identifying a biological in vivo function. Breast cancer is the third commonest cancer in the world and the commonest malignant disease of women. The expression of functional NIS may therefore be useful in the radioiodide diagnosis and therapy of responsive tumors of the breast (see reviews by A. De La Vieja et al., Physiol Rev. 2000 July 80 (3):1083-105; C. Riedel et al., Trends Biochem Sci. 2001 Aug. 26 (8): 490-6; A. E. Heufelder et al., Thyroid. 2001 Sep. 11 (9): 839-47).

Factors which modulate NIS expression and iodide uptake in breast cancer cells have not to date been investigated in detail. There has recently been a report of the induction of the NIS gene by trans-retinoic acid (tRA) in the breast cancer cell line MCF-7. It was suggested that the tRA-induced NIS expression is stimulated by two families of nuclear receptors, namely retinoic acid receptors (RARs) and retinoid X receptors (RXRs) (T. Kogai et al., Proc Natl Acad Sci USA. 2000 July 97 (15): 8519-24). MCF-7 cells express not only functional RAR/RXR but also nuclear PPAR-γ (peroxisome proliferator activated receptor-γ) (M. W. Titcomb et al. Mol Endocrinol. 1994 Jul. 8 (7): 870-7; M. W. Kilgore et al., Mol Cell Endocrinol. 1997 May 129 (2): 229-35). PPAR-γ regulates, in the presence of appropriate ligands, through heterodimerization with RAR/RXR (RXRα, RXRβ or RXRγ) the transcription of target genes (M. Sato et al. Biochem Biophys Res Commun. 2001 January. 280 (3): 646-51). PPAR-γ and RAR/RXR are co-expressed in various malignant epithelial tumors such as carcinomas of the brain, breast, prostate and lung (J. O. Nwankwo and M. E. Robbins, Prostaglandins Leukot Essent Fatty Acids. 2001 April-May 64 (4-5): 241-5; K. Inoue et al., Anticancer Res. 2001 July-August 21 (4A): 2471-6).

The present invention shows that iodide uptake in cells of certain carcinomas can be considerably increased by a simultaneous or sequential action of PPAR-γ ligands and RAR/RXR ligands, with a multiple potentiation by the PPAR-γ ligands of the iodide uptake induced by the RAR/RXR ligands. This synergism is attributable to a heterodimerization of the PPAR-γ and RAR/RXR receptors and an NIS gene expression which is induced or stimulated and/or enhanced thereby. An increase, brought about in this way, of the iodide uptake into the cell is utilized according to the invention for the diagnosis and therapy of NIS-expressing primary carcinomas and metastases, especially primary tumors and/or metastases of glandular carcinomas, especially of carcinomas of the thyroid, of the salivary gland, of the uterus and of carcinomas of the breast, and other glandular carcinomas.

To detect induction of NIS gene expression in the selected carcinomas by the heterodimerizing PPAR-γ and RAR/RXR receptors, the present invention investigated in particular the effect of, for example, ciglitazone (CIG), a synthetic PPAR-γ ligand, on iodide uptake by MCF-7 cells with and without addition of trans-RA (tRA). The breast cancer cell line MCF-7 expresses the PPAR-γ and RAR/RXR receptors (M. W. Kilgore et al., Mol Cell Endocrinol. 1997 May 129 (2): 229-35). It was possible to show according to the invention that the receptors activated by the appropriate ligands synergistically induce or stimulate and/or enhance NIS gene expression, and thus enhance the function of NIS.

Ciglitazone (CIG) is a substance belonging to the class of synthetic thiazolidinediones (TZDs) which represent the most potent PPAR-γ inducers (G. J. Murphy and J. C. Holder, Trends Pharmacol Sci. 2000 December. 21 (12): 469-74). This substance has been described as selective activator of PPAR-γ (Y. Sugiyama et al., Nippon Rinsho. 2000 February. 58 (2): 370-5).

Figure 1:
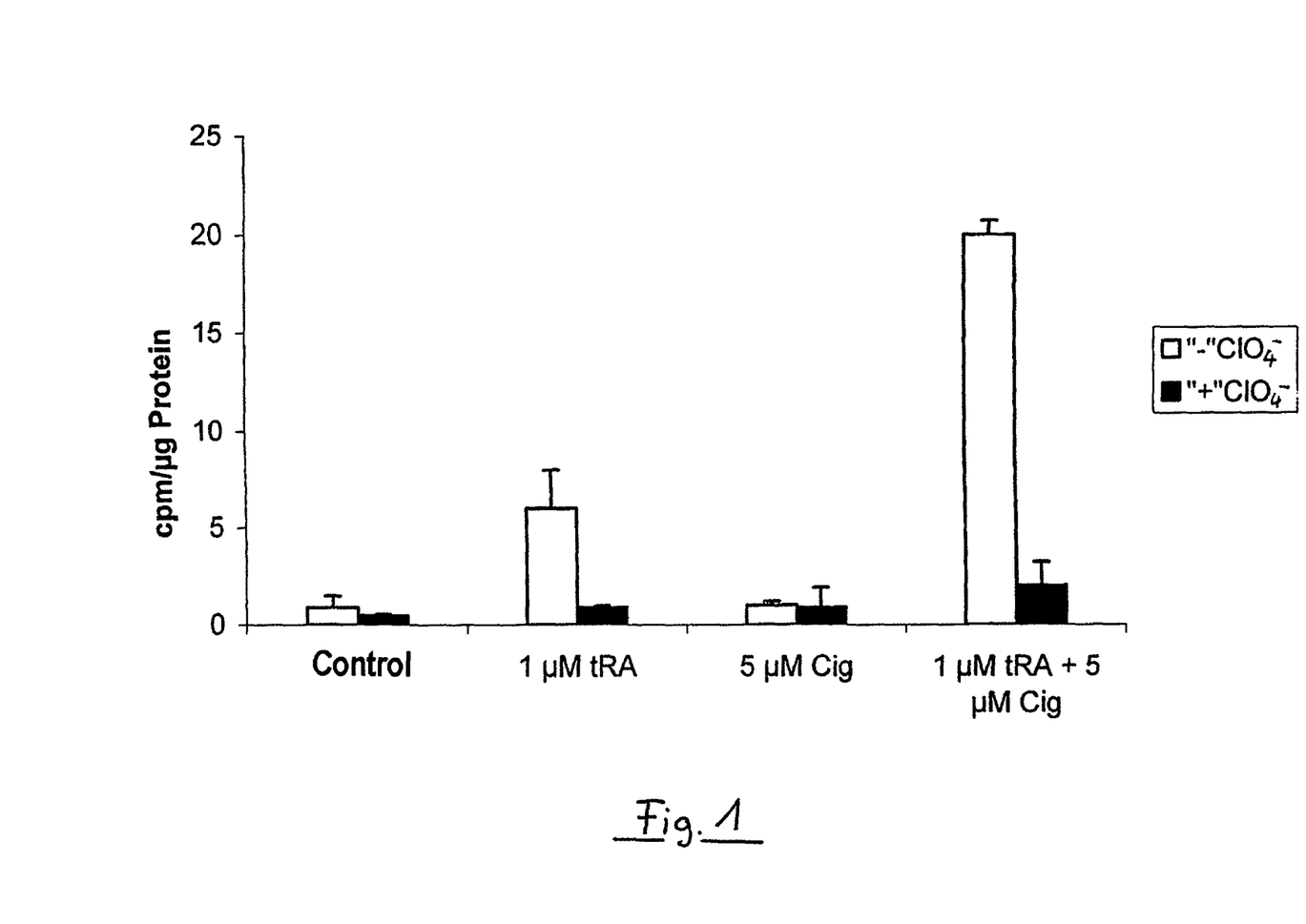
FIG. 1 the effect of CIG on the tRA-induced iodide uptake in breast cancer cells. The cells were treated with 1 μM tRA with or without 5 μM CIG for 48 h, and the iodide uptake assay was carried out with (black rectangles) or without (white rectangles) 30 mM $KClO_4$. The values have been expressed as means±SD (n=3)
Figure 2:
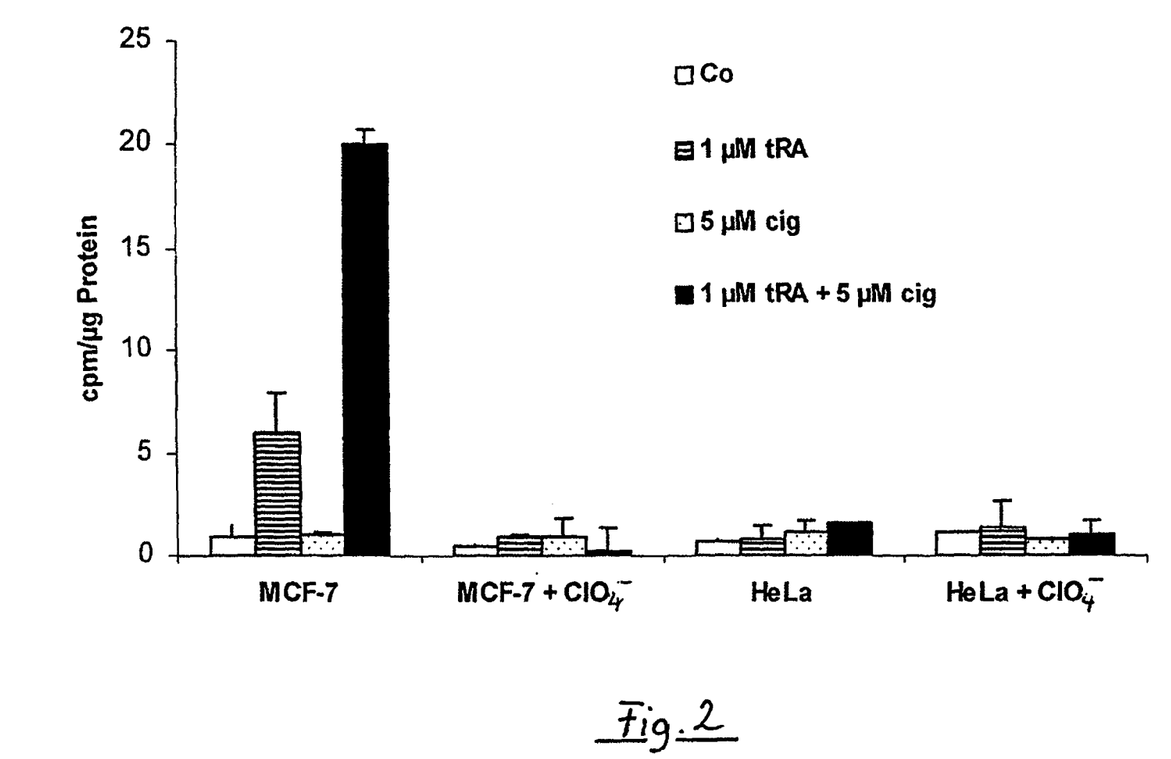
FIG. 2 the cell-specific effect of tRA and CIG on iodide uptake. MCF-7 and HeLa cells were treated with 1 μM tRA with or without 5 μM CIG for 24 h. The iodide uptake assay was carried out in the presence or absence of 30 mM $KClO_4$ for 1 h. The values have been expressed as means±SD (n=3).

The present invention shows that CIG in combination with tRA distinctly enhances iodide uptake in the breast cancer cell line MCF-7 compared with the iodide uptake induced or increased by tRA alone, whereas CIG alone shows no effect (FIG. 1). The NIS expression induced by CIG and tRA, or the iodide uptake brought about thereby, is specific for MCF-7 cells. For example, no iodide uptake was observable in the cervical carcinoma cell line HeLa after treatment over 48 hours with CIG and tRA (FIG. 2).

Treatment of MCF-7 cells with tRA alone increases iodide uptake by about 6-fold. However, combination of tRA with CIG increases iodide uptake by about 20-fold compared with untreated cells (FIG. 1). Simultaneous treatment of the breast cancer cells with CIG and tRA thus brings about a more than 3-fold increase in the iodide uptake compared with cells treated only with tRA. CIG alone does not induce iodide uptake in MCF-7 cells. It has additionally been shown according to the invention that the concentration of NIS mRNA is distinctly increased by treating the cells with tRA, demonstrating an effect of the substances at the level of transcription. These results show that NIS gene expression is increased synergistically by treatment of CIG in combination with retinoic acid in the breast cancer cell line MCF-7.

It is known from earlier investigations that trans-retinoic acid (tRA) induces iodide uptake in MCF-7 cells by stimulating NIS expression, the effect of tRA being mediated by the RAR/RXR receptors (T. Kogai et al., Proc Natl Acad Sci USA. 2000 July 97 (15): 8519-24). The results which have led to the present invention show the presence of functional responsive elements for the PPAR-γ and RAR/RXR receptors in cancer cells, with the responsive elements and the receptors synergistically interacting with one another. The observation that the increase, induced by a simultaneous action of CIG and tRA, in NIS expression is specific to MCF-7 cells and does not take place in, for example, HeLa cells (FIG. 2) shows the selectivity of the described mechanism for particular cancer cells. This result is consistent with the previously described observation that tRA does not induce iodide uptake in other cancer cell lines, such as the prostate cancer cell line LNCaP, the choriocarcinoma cell line JEG-3 or two non-small-cell lung cancer cell lines A549 and H460 (T. Kogai et al., Proc Natl Acad Sci USA. 2000 July 97 (15): 8519-24).

On the basis of the described results, a method for diagnosing and/or treating sodium-iodide symporter (NIS)-expressing carcinomas and/or metastases is proposed according to the invention. In this method there is organ-specific stimulation of an induction or increase in NIS gene expression in said types of tumor and enhanced iodide uptake, which is utilized according to the invention for a specific diagnosis and/or a targeted therapy.

The method of the invention can be employed particularly preferably for the diagnosis and/or treatment of glandular carcinomas, especially carcinomas of the salivary gland, of the thyroid, of the uterus and of breast cancer or carcinomas of the breast, and/or the corresponding metastases.

The induced or increased NIS gene expression is utilized according to the invention for introducing, through the enhanced expression or function of the sodium-iodide symporter, preferably radioactive substances into the tumor cells. The radioactivity can be utilized as a very sensitive indicator in the diagnosis by means of scintigraphic methods and/or as active therapeutic agent in the therapy by means of radiolysis. Radiolysis means destruction of the cells by radioactive radiation. A particular advantage of radiolysis is that, even with only a very small uptake of radioiodide, the radiolytic effect is, owing to the range of the radiation, transferred to neighboring cells as so-called bystander effect.

The substances preferably employed according to the invention are those having a high affinity for the NIS symporter, especially iodine and/or technetium. However, other substances with affinity, especially from the halogen group, can also be used. The use of radioiodide and/or technetium, especially radioactive technetium, after preferably systemic use of the NIS gene-inducing active compounds, i.e. in particular the PPAR-γ and RAR/RXR ligands, proves according to the invention to be particularly valuable means for the diagnosis and treatment of the tumors indicated above. It is possible and particularly advantageous to use as radioactive iodine for this purpose $^{123}$I, $^{125}$I and/or $^{131}$I, especially in the form of an alkali metal or alkaline earth metal iodide, for example sodium iodide (NaI). In this connection, $^{125}$I is particularly advantageously employed for diagnosis, and $^{131}$I is particularly advantageously employed for therapy.

The term "iodide uptake" hereinafter also means uptake of other substances which have an affinity for the NIS symporter and can be actively transported by it. Addition of the substance whose transport by the sodium-iodide symporter is to be detected or which is intended to cause radiolysis advantageously takes place after an appropriate time after administration of the active compounds which serve to stimulate and/or enhance NIS gene expression. An appropriate time may in this connection be for example about 1 to 5 days, preferably about 1 to 3 days. About 2 days are particularly preferred.

In a preferred embodiment of the method of the invention, NIS gene expression is induced by means of a treatment with at least one PPAR ligand, especially a PPAR-γ ligand, and at least one RAR/RXR ligand as active compounds, in which case the iodide uptake which is increased by the RAR/RXR ligand is potentiated in a synergistic manner by the PPAR-γ ligand. It is particularly preferred in this connection for the ligands for the two types of receptors to be administered sequentially, with the at least one RAR/RXR ligand preferably being administered first and the at least one PPAR ligand being administered after an appropriate time. The intention is that initial induction of NIS gene expression takes place in this time. It is additionally possible through the sequential administration to abolish a blockade of the PPAR-γ, which may be brought about by a suppressor, by an RAR/RXR activated with an appropriate ligand, so that the PPAR-γ ligand can subsequently have a maximal effect. A suitable pretreatment with an RAR/RXR ligand, in particular with retinoic acid, can advantageously be carried out over a few hours up to some days. 1 to 3 days are particularly preferred, especially 2 days. Such a pretreatment can take place for example through an appropriate infusion and/or through single or multiple oral administration of the appropriate active compound. In addition, initial administration of the at least one PPAR-γ ligand, and sequential administration of the at least one RAR/RXR ligand may also be preferred. Simultaneous administration of ligands for both types of receptors may likewise lead to the desired result and be preferred.

Ligands preferably used for the PPAR-γ receptor are active compounds from the class of thiazolidinediones, especially ciglitazone, pioglitazone, rosiglitazone or mixtures thereof. The ligand preferably employed for the RAR/RXR receptors is retinoic acid and/or at least one pharmacologically acceptable derivative thereof, especially trans-retinoic acid and/or at least one derivative thereof. This derivative may be for example a salt or an ester, in particular an ester with an alkanoic acid preferably having 1 to 4 C atoms.

In a further embodiment of the invention, besides the PPAR-γ and RAR/RXR ligands described above it is also possible to employ additional substances which have a modulating, in particular activating, effect on the activity of the active compounds. These substances are preferably activators, in particular coactivators, which are able for example to form a complex with the two types of receptors. Substances suitable for this purpose are those able to take part as further receptor in the complex formation and which have an activating effect on NIS gene expression in the sense according to the invention.

It is additionally possible by administering suitable substances to attenuate and/or eliminate the effect of cell-intrinsic substances which act in particular as suppressors to inhibit the activation of NIS gene expression by PPAR ligands and RAR/RXR ligands, so that NIS gene expression can be increased according to the invention. Examples of such suppressors which inhibit activation of NIS gene expression are the liver lipid receptor (LXR) and/or the thyroid hormone receptor (Ide T. et al., Molecular Endocrinology, May 2003; Behr M. and U. Loos, Exp Clin Endocrinol Diabetes 1996 (104) Suppl 4: 111-6). These receptors and/or corresponding agonists, e.g. ligands of these receptors, attenuate or suppress the heterodimerization of PPAR-γ and RAR/RXR. Administration of antagonists of these receptors having a suppressant effect eliminates or blocks these suppressors according to the invention, and thus enhances the interaction of PPAR-γ and RAR/RXR and therefore increases their effect according to the invention on NIS gene expression and function. Examples of antagonists which can be employed are those ligands of the liver lipid receptor and/or thyroid hormone receptor which block the activity thereof. Examples of such antagonists, especially of thyroid hormone receptor antagonists, are TRIAC and/or TETRAC.

A further possibility is also to employ as activator for example a histone deacetylase inhibitor, in particular trichostatin A and/or a butyrate. It is known of histone deacetylase inhibitors that it increases NIS expression in a moderately differentiated thyroid carcinoma cell line (M. Kitazono et al., J. Clin Endocrinol Metab. 2001 July 86 (7): 3430-5). Alternatively, suppressors which downregulate in particular the expression of the NIS gene can be eliminated or blocked by suitable substances.

Targeted induction of NIS gene expression for the diagnosis and/or therapy of said types of tumors can also be achieved according to the invention with other active compounds. These active compounds may be hormones or other ligands for particular receptors which are expressed on the surface of the cells of the indicated metastases or carcinomas. An example which should be mentioned of such active compounds is prolactin, which is known to be able to modulate iodide uptake in lactating mammary gland cells.

A particularly preferred embodiment of the diagnostic method of the invention includes an in vivo diagnosis. For this purpose, at least one ligand for the PPAR-γ receptor, e.g. a thiazolidinedione such as, for example, ciglitazone, and at least one ligand for the RAR and/or RXR receptor, e.g. trans-retinoic acid, is administered to the patient to be investigated. Oral or parenteral administration is preferred. Intravenous administration of the substances is likewise possible. Preferably after an appropriate time during which induction of the NIS gene takes place, a suitable dose of a further substance, in particular technetium and/or radioactive iodine, e.g. $^{131}$iodine, is administered. This time is advantageously about 1 to about 5 days, preferably about 1 to about 3 days. About 2 days are particularly preferred. Preferably after a further appropriate period of time, which is suitable for iodide uptake or, for example, technetium uptake in cells, the uptake of the substance into the cells is analyzed. This takes place for example by a whole-body scintigram or a local scintigram, for example of the breast, to detect primary tumors and/or metastases. Since the iodide uptake after such a treatment is potentiated according to the invention only in NIS-expressing cells, the in vivo diagnostic method of the invention makes specific indication of tumors possible. With this method it is possible to detect specifically even very small tumors or micrometastases which have a diameter of less than 0.5 cm and can, for example, still be curatively treated. This shows a further particular advantage of the method of the invention, since detection of such micrometastases is usually not possible with conventional diagnostic methods.

An analysis of the abovementioned types of cancer can also take place according to the invention by an in vitro diagnostic method. This can particularly preferably be used for establishing and/or optimizing the dose of the active compounds and/or substances to be administered, especially of the corresponding receptor ligands, for the subsequent therapy. The in vitro diagnostic method can include for example the following steps. The cells of a sample to be investigated, for example a sample resected surgically, are initially incubated with, for example, at least one ligand for the PPAR-γ receptor, e.g. a thiazolidinedione, and at least one ligand for the RAR and/or RXR receptor, e.g. trans-retinoic acid. Subsequently, cells thus prepared are treated with, for example, radioactive iodine and/or technetium. The conditions for this should permit uptake of the iodine or technetium by the cells and are known to the skilled worker. Finally, the content or the concentration of the transported iodine or technetium in the cells can be determined. Measurement of the radioactive iodine or technetium can be carried out by known methods, such as, for example, in a gamma counter. Alternatively, instead of incubation with a source of radioactive iodine or technetium and subsequent measurement of the radioactivity, it is also possible to measure expression of the NIS mRNA in the cells of the sample to be investigated after the treatment with the active compounds or ligands for the PPAR-γ and RAR/RXR receptors. In this case, the expression of NIS mRNA can be determined by means of a reverse transcriptase polymerase chain reaction (RT-PCR) or other methods known in the art.

A therapeutic method of the invention for treating the indicated types of cancer may include for example the following steps. Initially active compounds able to induce NIS gene expression in said types of tumors are administered to the patient to be treated. It is particularly preferred to administer, in particular orally and/or parenterally, for this purpose at least one ligand for the PPAR-γ receptor, e.g. a thiazolidinedione, in combination with one or more ligands for the RAR and/or RXR receptor, e.g. trans-retinoic acid. Intravenous administration of the active compounds is likewise possible. The ligands can be administered simultaneously or sequentially. After an appropriate time during which the NIS gene is induced, a suitable dose of a substance intended to bring about radiolysis of the tumor cells is administered. Radioactive iodide, e.g. $^{131}$iodide, is particularly preferred in this connection. Neither in the therapy nor in the described diagnostic methods is it absolutely necessary to wait an appropriate time before administering for example radioactive iodine. It is likewise possible for the administration of the ligands and the administration of iodine for example to take place simultaneously. The described steps are repeated if necessary at suitable time intervals, e.g. between 7 and 14 days. The radioiodide uptake takes place according to the invention organ-specifically, mainly in the cells of the indicated types of tumors, in which NIS expression is potentiated and iodide uptake is enhanced through the treatment. In contrast to a systemic radiotherapy known in the art, the tumor cells of the specified carcinomas and metastases are addressed specifically with the therapeutic method of the invention. The progress and success of treatment can be followed for example using the in vivo and/or in vitro diagnostic methods described above. The therapy of the invention can particularly advantageously take place after surgical removal of primary tumors, in order thus to be able to control metastases successfully. In some circumstances, it may also be preferred to employ the therapy of the invention instead of an operation or possibly before an operation. This is advantageous especially when an operation does not come under consideration for any reasons.

The present invention additionally relates to pharmacological compositions and products comprising active compounds able to induce, stimulate and/or enhance NIS gene expression in said types of tumors. Such compositions preferably comprise as active compounds ligands for the PPAR, especially PPAR-γ, and RAR and/or RXR receptors. Compositions advantageous in this connection are those comprising at least one active compound from the class of thiazolidinediones and retinoic acid and/or its derivatives, especially trans-retinoic acid. It is additionally possible for such compositions according to the invention to include further substances, preferably activators, especially coactivators, of the NIS gene and/or histone deacetylase inhibitors, which likewise have a stimulating effect on NIS expression. In this regard, reference is made to the above description. The compositions or products may additionally include at least one pharmacologically acceptable carrier and/or excipient. Such compositions or products can be employed according to the invention as diagnostic aids and/or as medicaments for diagnosing and/or treating primary carcinomas and/or metastases, especially glandular carcinomas, preferably carcinomas of the thyroid, of the salivary gland, of the uterus and/or carcinomas of the breast, and the corresponding metastases.

The invention further includes a kit, in particular for the diagnosis and/or therapy of NIS gene-expressing carcinomas and/or metastases, which comprises active compounds able to induce, stimulate and/or enhance NIS gene expression in the tumors. This kit particularly preferably comprises at least one ligand for the PPAR-γ receptor, in particular a thiazolidinedione such as, for example, ciglitazone, and at least one ligand for the RAR and/or RXR receptor, in particular a trans-retinoic acid. The kit may additionally comprise a source of radioactive iodine and/or technetium. The kit may additionally comprise substances having a modulating effect, preferably activators, in particular coactivators. In this regard, reference is made to the description above. Particularly preferred as activator in this connection is a histone deacetylase inhibitor, in particular trichostatin A or a butyrate. Concerning further features of the composition and products of the invention, reference is likewise expressly made to the description above.

Finally, the invention includes a use of at least one PPAR ligand, in particular a PPAR-γ ligand, and of at least one RAR and/or RXR ligand for producing a diagnostic composition for the detection or for producing a medicament for the treatment of carcinomas and/or metastases which express an NIS gene. These carcinomas and/or metastases are in particular primary tumors and/or metastases of glandular carcinomas, in particular of salivary gland carcinomas, thyroid carcinomas, uterine carcinomas and/or carcinomas of the breast.

In a preferred embodiment of this aspect of the invention, the at least one PPAR-γ ligand comprises one or more thiazolidinediones, in particular ciglitazone, pioglitazone and/or rosiglitazone. The at least one RAR and/or RXR ligand is advantageously retinoic acid, in particular trans-retinoic acid, and/or one or more pharmacologically acceptable derivatives thereof. An appropriate pharmacologically acceptable derivative is advantageously a salt and/or an ester of retinoic acid, in particular an ester with an alkanoic acid preferably having 1 to 4 C atoms.

A particularly preferred embodiment of the use according to the invention provides for employing the diagnostic composition and/or the medicament for combination with a substance which is actively transported by the NIS symporter. Expression of the NIS gene is induced or stimulated and/or enhanced by the use of the described ligands, so that ultimately an increased activity of this symporter in the affected cells, and thus an enhanced uptake of iodine or of other substances for which the symporter has an affinity is to be observed. This enhanced activity of the symporter is utilized according to the invention for diagnosis or therapy by detecting the uptake of the affinity substance into the cell, or by bringing about through the uptake of, for example, radioactive affinity substances a radiolysis and thus a destruction of the affected cells. The affinity substances claimed are in particular halides, and in this connection particularly preferably iodine. A further preferred affinity substance is, for example, technetium.

In a particularly preferred embodiment of this aspect of the use according to the invention, the radioactive substance is radioactive iodine, preferably $^{123}$I, $^{125}$I and/or $^{131}$I. It is particularly preferred for the iodine, in particular the radioactive iodine, to be in the form of an iodide, preferably in the form of an alkali metal and/or alkaline earth metal iodide. Sodium iodide (NaI) is particularly advantageous in this connection.

In a further advantageous embodiment of the uses according to the invention, the diagnostic composition or the medicament is configured so that the at least one RAR/RXR ligand is administered first, and the at least one PPAR ligand is administered after an appropriate time. Such a sequential administration has the advantage that the synergistic effect of the two ligands or of the two ligand groups can be enhanced, which may derive in particular from initial suppression of the PPAR-γ receptor in its activity for example through the presence of suppressors. The activation of RAR/RXR by the appropriate ligand(s) also converts PPAR-γ into an active form, so that the full synergistic effect can be achieved through the subsequent administration of ligands for PPAR-γ. On the other hand, it may also be advantageous initially to administer at least one PPAR ligand, in particular at least one PPAR-γ ligand, and later to administer at least one RAR/RXR ligand. Administration of the ligand groups at the same time may also be preferred. Concerning further features of these uses according to the invention, reference is expressly made to the above description.

Besides the described the use of said ligands for producing a diagnostic composition or for producing a medicament, the invention likewise includes the use of at least one PPAR ligand, in particular a PPAR-γ ligand, and at least one RAR and/or RXR ligand for the diagnostic detection or for the treatment of carcinomas and/or metastases which express an NIS gene. Concerning further features of this aspect of the invention, reference is made to the above description.

The described method of the invention for the diagnosis and therapy of the types of tumors indicated above, and the relevant compositions, products and uses have the advantage compared with known methods and compositions inter alia that they make specific identification of primary tumors and/or their metastases, and an efficient and tumor-specific radioiodine therapy, possible.

Further advantages, features and possible uses of the invention are described below by means of the exemplary embodiments with reference to the drawings. In this connection, the various features may in each case be implemented on their own or in combination with one another. The drawings show.

EXAMPLES

All the cell lines used herein were purchased from the Deutschen Sammlung von Mikroorganismen und Zelikulturen (DSMZ; Brunswick, Germany, DSMZ No.: MCF-7 (ACC 115)). MCF-7 cells were cultured in RPMI 1640 medium with 10% FCS (fetal calf serum) and addition of 1× nonessential amino acids, 0.01 mg/ml bovine insulin and 5% penicillin/streptomycin. The HeLa cells were cultured in RPMI 1640 medium. All the reagents for the cell culture were, unless indicated otherwise, purchased from Invitrogen, Karlsruhe, Germany.

The experiments were statistically analyzed with the paired T test using the program from Statview, version 5.0 (SAS Institute Inc. USA).

Iodide Uptake Experiments

Cells were cultured in plates with 24 wells (24 Well Plates) for 24 h. The cells were then washed and subsequently the substances to be tested (ciglitazone, trans-retinoic acid with or without $KClO_4$) were added in fresh medium. For the iodide uptake, the cells were first washed twice in prewarmed RPMI 1640 medium without FCS, and then incubated in 1 ml of RPMI 1640 without FCS which comprised 0.1 μCi/ml $Na^{125}I$ (specific activity: 10 mCi/mmol, Amersham Biosciences, Freiburg, Germany) and 10 μM NaI/well for 1 h.

After the incubation, the cells were washed twice with ice-cold RPMI 1640 and lysed in 2% SDS-PAGE sample buffer (0.0625 M Tris-HCl, pH 6.8) with 1 U/μl Benzonase (Merck KgaA, Darmstadt, Germany). The $^{125}I$ uptake was measured in a gamma counter. An aliquot of each sample was employed to determine the protein concentration using the DC protein determination kit from Bio-Rad (Munich, Germany) in order thus to achieve standardization with different numbers of cells.

MCF-7 cells were firstly treated with 1 μM trans-retinoic acid (tRA) (Sigma, Munich, Germany) in the presence or absence of 5 μM CIG (Bio-mol, Hamburg, Germany) for 48 h at different time intervals. The maximum uptake was reached with 1 μM tRA after 48 h. The iodide uptake assay showed that simultaneous treatment of the cells with tRA and CIG allows the iodide uptake which is increased 5-fold by tRA to be raised further (potentiated) by 3.3-fold (FIG. 1).

Induction of iodide uptake by combined stimulation with CIG and tRA was also tested in HeLa cells in order to show the specific effect of these substances on MCF-7 cells. HeLa cells were treated with 1 μM tRA with or without 5 μM CIG for 48 h. Compared with MCF-7 cells, no induction of iodide uptake was observed in HeLa cells after treatment with tRA, CIG and tRA combined with CIG for 48 h (FIG. 2). The same results were obtained when HEK-293 cells were employed in an analogous experiment (results not shown). These results show the specific effect on iodide uptake in MCF-7 cells by CIG in combination with tRA.

Viability of the cells was not impaired by the treatment with CIG and tRA, as shown by Trypan blue staining (results not shown).

Blocking Experiments

In order to test the specificity of NIS-mediated iodide uptake, the experiments described in the previous exemplary embodiment were also carried out in the presence of 30 mM $KClO_4$, the strongest specific NIS inhibitor.

The iodide uptake was inhibited by $KClO_4$ (FIG. 1), indicating a specific NIS-mediated iodide uptake by the breast cancer cells.

These results show that the tRA-induced iodide uptake is multiplied by CIG and that this is mediated by the specific function of NIS.

The present invention is not restricted to the use examples described above. On the contrary, many modifications are possible and can be achieved by skilled workers, and are thus within the scope of this invention.

REFERENCES

Carrasco N. Iodide transport in the thyroid gland. Biochim Biophys Acta. 1993 Jun. 8; 1154(1):65-82.

De La Vieja A, Dohan O, Levy O, Carrasco N. Molecular analysis of the sodium/iodide symporter; impact on thyroid and extrathyroid pathophysiology. Physiol Rev. 2000 July; 80(3):1083-105.

Heufelder A E, Morgenthaler N, Schipper M L, Joba W. Sodium iodide symporter-based strategies for diagnosis and treatment of thyroidal and nonthyroidal malignancies. Thyroid. 2001 September; 11(9):839-47.

Inoue K, Kawahito Y, Tsubouchi Y, Yamada R, Kohno M, Hosokawa Y, Katoh D, Bishop-Bailey D, Hla T, Sano H. Expression of peroxisome proliferator-activated receptor (PPAR)-gamma in human lung cancer. Anticancer Res. 2001 July-August; 21(4A):2471-6.

Kilgore M W, Tate P L, Rai S, Sengoku E, Price T M. MCF-7 and T47D human breast cancer cells contain a functional peroxisomal response. Mol Cell Endocrinol. 1997 May 16; 129(2):229-35.

Kitazono M, Robey R, Zhan Z, Sarlis N J, Skarulis M C, Aikou T, Bates S, Fojo T. Low concentrations of the histone deacetylase inhibitor, depsipeptide (FR901228), increase expression of the Na(+)/I(−) symporter and iodine accumulation in poorly differentiated thyroid carcinoma cells. J Clin Endocrinol Metab. 2001 July; 86(7):3430-5.

Kogai T, Schultz J J, Johnson L S, Huang M, Brent G A. Retinoic acid induces sodium/iodide symporter gene expression and radioiodide uptake in the MCF-7 breast cancer cell line. Proc Natl Acad Sci USA. 2000 Jul. 18; 97(15):8519-24.

Mazzaferri E L, 1996 in The Thyroid, eds. Braverman L E and Utiger R D (Lippincott-Raven, Philadelphia), pp. 942-945.

Murphy G J, Holder J C. PPAR-gamma agonists: therapeutic role in diabetes, inflammation and cancer. Trends Pharmacol Sci. 2000 December; 21 (12):469-74. Review.

Nwankwo J O, Robbins M E. Peroxisome proliferator-activated receptor-gamma expression in human malignant and normal brain, breast and prostate-derived cells. Prostaglandins Leukot Essent Fatty Acids. 2001 April-May; 64(4-5): 241-5.

Riedel C, Dohan O, De la Vieja A, Ginter C S, Carrasco N. Journey of the iodide transporter NIS: from its molecular identification to its clinical role in cancer. Trends Biochem Sci. 2001 August; 26(8):490-6.

Sato M, Yajima Y, Kawashima S, Tanaka K, Kagechika H. Synergistic potentiation of thiazolidinedione-induced ST 13 preadipocyte differentiation by RAR synergists. Biochem Biophys Res Commun. 2001 Jan. 26; 280(3):646-51.

Sugiyama Y, Murase K, Ikeda H. Mechanisms of thiazolidinedione derivatives for hypoglycemic and insulin sensitizing effects. Nippon Rinsho. 2000 February; 58(2):370-5. Review. Japanese.

Tazebay U H, Wapnir I L, Levy O, Dohan O, Zuckier L S, Zhao Q H, Deng H F, Amenta P S, Fineberg S, Pestell R G, Carrasco N. The mammary gland iodide transporter is expressed during lactation and in breast cancer. Nat Med. 2000 August; 6(8):871-8.

Titcomb M W, Gottardis M M, Pike J W, Allegretto E A. Sensitive and specific detection of retinoid receptor subtype proteins in cultured cell and tumor extracts. Mol Endocrinol. 1994 July; 8(7):870-7.

The invention claimed is:

1. A method for diagnosing NIS gene-expressing carcinomas, metastases of carcinomas or both by stimulating or enhancing NIS gene expression in cells of the carcinomas or the metastases thereby increasing NIS-symporter function, comprising:
administering to a patient in need thereof at least one PPAR-γ ligand that is a thiazolidinedione, at least one ligand selected from the group consisting of RAR ligand and RXR ligand, and a radioactive affinity containing substance actively transported by the NIS symporter into cells of the carcinomas or the metastases; and
stimulating or enhancing uptake of the radioactive affinity containing substance actively transported by the NIS symporter by induction of NIS gene expression in the cells.

2. A method for treating NIS gene-expressing carcinomas, metastases of carcinomas or both by stimulating or enhancing NIS gene expression in cells of the carcinomas or the metastases thereby increasing NIS-symporter function, comprising:
administering to a patient in need thereof at least one PPAR-γ ligand that is a thiazolidinedione, at least one ligand selected from the group consisting of RAR ligand and RXR ligand, and a radioactive affinity containing substance actively transported by the NIS symporter into cells of the carcinomas or the metastases; and
stimulating or enhancing uptake of the radioactive affinity containing substance actively transported by the NIS symporter by induction of NIS gene expression in the cells.

3. The method of claim 1, wherein the NIS gene-expressing carcinomas, metastases of carcinomas or both thereof are selected from the group consisting of primary tumors, metastases of glandular carcinomas, salivary gland carcinomas, thyroid carcinomas, uterine carcinomas, and carcinomas of the breast.

4. The method of claim 1, wherein the at least one PPAR-γ ligand that is a thiazolidinedione is selected from the group consisting of ciglitazone, pioglitazone, rosiglitazone and mixtures thereof.

5. The method of claim 1, wherein the at least one ligand selected from the group consisting of RAR ligand and RXR ligand is retinoic acid or a salt or an ester thereof.

6. The method of claim 1, wherein the retinoic acid is trans-retinoic acid.

7. The method of claim 6, wherein the ester is an ester with an C1 to C4 alkanoic acid.

8. The method of claim 1, wherein the radioactive affinity containing substance is a halogen.

9. The method of claim 8, wherein the halogen is iodine selected from the group consisting of an alkali metal iodide, alkaline earth metal iodide and radioactive iodine.

10. The method of claim 9, wherein the iodine is sodium iodide.

11. The method of claim 9, wherein the iodine is $^{123}$I, $^{125}$I or $^{131}$I.

12. The method of claim 1, wherein the radioactive affinity containing substance is technetium.

13. The method of claim 1, wherein the at least one ligand selected from the group consisting of RAR ligand and RXR ligand is administered first and the at least one PPAR-γ ligand that is a thiazolidinedione is administered after an appropriate time ranging from about some hours to some days.

14. The method of claim 13, wherein the appropriate time is about 1 to about 3 days.

15. The method of claim 1, wherein metastases with a diameter of less than about 1 cm are diagnosed.

16. The method of claim 15, wherein metastases with a diameter of less than about 0.5 cm are diagnosed.

17. The method of claim 2, wherein the NIS gene-expressing carcinomas, metastases of carcinomas or both thereof are selected from the group consisting of primary tumors, metastases of glandular carcinomas, salivary gland carcinomas, thyroid carcinomas, uterine carcinomas, and carcinomas of the breast.

18. The method of claim 2, wherein the at least one PPAR-γ ligand that is a thiazolidinedione is selected from the group consisting of ciglitazone, pioglitazone, rosiglitazone and mixtures thereof.

19. The method of claim 2, wherein the at least one ligand selected from the group consisting of RAR ligand and RXR ligand is retinoic acid or a salt or an ester thereof.

20. The method of claim 2, wherein the retinoic acid is trans-retinoic acid.

21. The method of claim 20, wherein the ester is an ester with an C1 to C4 alkanoic acid.

22. The method of claim 2, wherein the radioactive affinity containing substance is a halogen.

23. The method of claim 22, wherein the halogen is iodine selected from the group consisting of an alkali metal iodide, alkaline earth metal iodide and radioactive iodine.

24. The method of claim 23, wherein the iodine is sodium iodide.

25. The method of claim 23, wherein the iodine is $^{123}$I, $^{125}$I or $^{131}$I.

26. The method of claim 2, wherein the at least one ligand selected from the group consisting of RAR ligand and RXR ligand is administered first and the at least one PPAR-γ ligand that is a thiazolidinedione is administered after an appropriate time ranging from about some hours to some days.

27. The method of claim 26, wherein the appropriate time is about 1 to about 3 days.

28. The method of claim 2, wherein metastases with a diameter of less than about 1 cm are diagnosed.

29. The method of claim 28, wherein metastases with a diameter of less than about 0.5 cm are diagnosed.

30. The method of claim 2, wherein the radioactive affinity containing substance is technetium.

\* \* \* \* \*